(12) United States Patent
Xiong et al.

(10) Patent No.: US 11,234,923 B2
(45) Date of Patent: Feb. 1, 2022

(54) COSMETIC COMPOSITION AND A CLEANING AND CARING PRODUCT COMPRISING THE SAME

(71) Applicant: Covestro Deutschland AG, Leverkusen (DE)

(72) Inventors: Xiaohui Xiong, Shanghai (CN); Haixiang Lu, Shanghai (CN)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 0 days.

(21) Appl. No.: 16/651,452

(22) PCT Filed: Oct. 12, 2018

(86) PCT No.: PCT/EP2018/077883
§ 371 (c)(1),
(2) Date: Mar. 27, 2020

(87) PCT Pub. No.: WO2019/073039
PCT Pub. Date: Apr. 18, 2019

(65) Prior Publication Data
US 2020/0281841 A1 Sep. 10, 2020

(30) Foreign Application Priority Data

Oct. 13, 2017 (CN) .......................... 201710951140.0
Dec. 7, 2017 (EP) ..................................... 17205997

(51) Int. Cl.
| *A61K 8/81* | (2006.01) |
| *A61K 8/84* | (2006.01) |
| *A61K 8/87* | (2006.01) |
| *A61Q 5/12* | (2006.01) |
| *A61Q 5/02* | (2006.01) |

(52) U.S. Cl.
CPC ................ *A61K 8/817* (2013.01); *A61K 8/87* (2013.01); *A61Q 5/02* (2013.01); *A61Q 5/12* (2013.01); *A61K 2800/5424* (2013.01); *A61K 2800/5428* (2013.01)

(58) Field of Classification Search
None
See application file for complete search history.

(56) References Cited

U.S. PATENT DOCUMENTS

| 9,539,444 B2 | 1/2017 | Kinoshita et al. |
| 2016/0175233 A1* | 6/2016 | Benn .................. A61Q 5/10 |
| | | 8/401 |

FOREIGN PATENT DOCUMENTS

| CA | 2719451 A1 | 10/2009 | |
| CN | 100415203 C | 9/2008 | |
| CN | 104042453 A | 9/2014 | |
| CN | 104666116 A | 6/2015 | |
| WO | WO-2012084340 A2 * | 6/2012 | ............... A61Q 5/12 |
| WO | WO 2012084340 A2 | 6/2012 | |

OTHER PUBLICATIONS

International Search Report, PCT/EP2018/077883, dated Mar. 13, 2019, Authorized officer: Ilknur Durand-Oral.

* cited by examiner

*Primary Examiner* — Brian Gulledge
(74) *Attorney, Agent, or Firm* — Jed C. Benson (57) ABSTRACT

The present invention relates to a cosmetic composition and a cleaning and caring product comprising the same, use and application method of the cleaning and caring product. The cosmetic composition comprises: a polymerization product, which is obtained by reacting a system comprising the following components: an anionic polymer, an amphoteric polymer and water, the weight ratio of the anionic polymer to the amphoteric polymer is in the range from 1:100 to 100:1 and the total weight of the anionic polymer and the amphoteric polymer is no less than 0.1 wt %, based on that the amount of the composition is 100 wt %; an optional cationic polymer; an optional active ingredient; an optional additive; and an optional cosmetically acceptable medium.

12 Claims, 1 Drawing Sheet

COSMETIC COMPOSITION AND A CLEANING AND CARING PRODUCT COMPRISING THE SAME

CROSS-REFERENCE TO RELATED APPLICATION

This application is a national stage application under 35 U.S.C. § 371 of PCT/EP2018/077883, filed Oct. 12, 2018, which claims the benefit of European Application No. 17205997, filed Dec. 7, 2017, and Chinese Application No. 201710951140, filed Oct. 13, 2017, each of which is incorporated herein by reference.

TECHNICAL FIELD

The present invention relates to a cosmetic composition and a cleaning and caring product comprising the same, use and application method of the cleaning and caring product.

BACKGROUND ART

Hair is fibrous appendage of human body and also an important part of human body, and has the function of heat preservation in winter, sunscreening in summer and prettifying personal image. As people's living standard improves, more and more people begin to persue beauty and fashion, and thus hair dyeing and perming are becoming increasingly popular. However, frequent hair dyeing and perming will harm hair's health, leading to such phenomena as coarse hair, hair forking or entanglement. Therefore, there is a need for hair care.

The purpose of hair care is to alleviate the phenomena of coarse hair, hair forking or entanglement, and to reduce damage that may be brought about during combing. As such, manufacturers have added active ingredients into hair cleaning and caring products, and made efforts to find methods for retaining sufficiently effective amount of active ingredients on the hair after the cleaning and caring product is rinsed away.

CN1633959A discloses a conditioner comprising a fatty alcohol, stearamidopropyl dimethyl amine, propylene glycol, dimethicone, polyoxyethylene ether-45, an organic acid, a mixture of dimethylol dimethyl hydantoin and 3-iodo-2-propynyl butyl carbamate, fragrance, disodium ethylene diamine tetraacetate and deionized water. Those ingredients impart excellent moisture retention, combability and are suitable for damaged hair.

CN102170854A discloses a conditioner, which is a gel formed with a higher alcohol, a cationic polymer, a polyol and/or polyethylene glycol, and the preparation method thereof. It is necessary to dilute the gel 3-15 times (in mass) with water prior to use.

CN104666116A discloses a conditioner comprising 8 parts of fatty alcohol polyoxyethylene ether, 0.7 part of glyceryl monostearate, 0.3 part of soya bean lecithin, 0.1 part of skin bacteriostat, 0.5 part of octadecanol, 1 part of propylene glycol, 0.5 part of fragrance, 0.3 part of antioxidant and water.

In order to retain active ingredients on hair, a substantial amount of silicone compounds or cationic polymers are used in all the above cleaning and caring products. However, the silicone compounds such as silicone polymers are insoluble in water and will adhere to the hair surface and thus cannot be washed away thoroughly. With repeated use of the cleaning and caring product, silicone polymers will continuously wrap onto the hair surface, which will make the active ingredients in the cleaning and caring product unable to be absorbed by the hair anymore and in turn make the hair ruptured, forked and even lost. The cationic polymers will also adhere to hair, thus making the hair heavy and greasy.

Therefore, there is a need for a cleaning and caring product, the active ingredients therein may remain on hair with a sufficiently effective amount after the hair is rinsed and thus makes the hair easy to comb, smooth, soft, moist and nourishing, while other ingredients in the cleaning and caring product other than the active ingredients are easy to be washed away without adhering to the hair to make hair feel greasy and heavy.

SUMMARY OF THE INVENTION

The objective of the present invention is to provide a cosmetic composition and a method for preparing the same, a cleaning and caring product comprising the cosmetic composition, use and application method of the cleaning and caring product.

The cosmetic composition according to the present invention comprises:
a polymerization product, which is obtained by reacting a system comprising the following components:
 an anionic polymer,
 an amphoteric polymer, and
 water,
 the weight ratio of the anionic polymer to the amphoteric polymer is in the range from 1:100 to 100:1 and the total weight of the anionic polymer and the amphoteric polymer is no less than 0.1 wt %, based on that the amount of the composition is 100 wt %;
an optional cationic polymer;
an optional active ingredient;
an optional additive; and
an optional cosmetically acceptable medium.

The phrase polymerization in connection with the polymerization product also covers systems of the mentioned components of an anionic polymer, an amphoteric polymer and water which do not undergo a chemical reaction but an aggregation of the different polymers. Thus, the phrase polymerization product covers chemical and physical interactions of different polymers.

According to the invention, the phrase cationic polymer also covers substances which do not have repeating units like a polymer normally has, but also covers molecules which have a molecular mass of more than 100 g/mol and have a cationic character.

According to one aspect of the present invention, there provides a method for preparing the composition as provided by the present invention, comprising the following steps:
mixing and reacting the system comprising the anionic polymer, the amphoteric polymer and water, to obtain the polymerization product; and
mixing the polymerization product; an optional cationic polymer; an optional active ingredient; an optional additive; and an optional cosmetically acceptable medium, to obtain the composition.

According to a further aspect of the present invention, there provides a cleaning and caring product, which is prepared from the composition as provided by the present invention.

According to another aspect of the present invention, there provides use of the cleaning and caring product as provided according to the present invention in the application to the hair for hair care.

According to yet another aspect of the present invention, there provides a method for hair care comprises applying the cleaning and caring product as provided according to the present invention to the hair.

The polymerization product in the cosmetic composition according to the present invention is semi-flocculent material with reticular pores. When the composition according to the present invention or the cleaning and caring product comprising the composition according to the present invention is applied to the hair surface, the active ingredients therein will fill into the pores of the polymerization product. After 5-10 minutes, the active ingredients will diffuse from the pores and deposit onto the hair surface, which will not be easily washed away during subsequent washing process. At the same time, as water evaporates, the polymerization product will form into film gradually, which will then be easily washed away during subsequent washing process and thus will not deposit onto the hair surface. Therefore, compared with traditional silicone-containing or cationic polymer-containing compositions, the composition according to the present invention can not only increase the deposition amount of the active ingredients in the composition on the hair surface, thus guaranteeing its effect on the surface; but also makes it possible that other ingredients in the composition are not easy to deposit on the hair, thus avoiding greasy and heavy feeling of hair. In addition, the composition according to the present invention is stable and easy to preserve.

BRIEF DESCRIPTION OF THE DRAWINGS

The appended drawings and examples in the present invention are merely illustrative rather than limiting.

The present invention is further described in detail hereinafter in combination with the appended drawings and specific embodiments.

DETAILED DESCRIPTION OF THE INVENTION

The present invention provides a cosmetic composition comprising: a polymerization product, which is obtained by reacting a system comprising the following components: an anionic polymer, an amphoteric polymer, and water, the weight ratio of the anionic polymer to the amphoteric polymer is in the range from 1:100 to 100:1 and the total weight of the anionic polymer and the amphoteric polymer is no less than 0.1 wt %, based on that the amount of the composition is 100 wt %; an optional cationic polymer; an optional active ingredient; an optional additive; and an optional cosmetically acceptable medium. The present invention also provides a method for preparing the composition, a cleaning and caring product comprising the composition, use and application method of the cleaning and caring product.

Cosmetic Composition
Polymerization Product
Anionic Polymer

The amount of the anionic polymer can be 0.1-10 wt %, further preferably 0.5-5 wt %, and most preferably 0.5-2.5 wt %, based on that the amount of the composition is 100 wt %.

The above amount of the anionic polymer refers to the actual weight of the active material of the anionic polymer, excluding the carrier.

The anionic polymer is an anionic polyurethane.

The anionic polyurethane can be obtained by reacting a system comprising one or more water-insoluble, non-water dispersible isocyanate functionalized polyurethane prepolymers and one or more isocyanate reactive compounds.

The anionic polyurethane may comprise at least one sulfonic acid and/or sulfonate group.

The sulfonate group is preferably sodium sulfonate group.

The anionic polyurethane may be linear or branched, most preferably linear.

The anionic polyurethane may have a number-average molecular weight of 100,000-500,000 g/mol, further preferably of 120,000-400,000 g/mol and most preferably of 150,000-450,000 g/mol.

Water-Insoluble, Non-Water Dispersible Isocyanate Functionalized Polyurethane Prepolymer The term "water-insoluble, non-water dispersible isocyanate functionalized polyurethane prepolymer" means that the prepolymer has a solubility in water of less than 10 g/L, preferably of less than 5 g/L at 23° C., and it is not able to produce a settlement-stable dispersion in water (especially deionized water) at 23° C. In other words, the prepolymer will precipitate during the experiment of dispersing it in water.

The water-insoluble, non-water dispersible isocyanate functionalized polyurethane prepolymer preferably has isocyanate end group(s), i.e., the isocyanate group is located at the end of the prepolymer chain. Most preferably, there is an isocyanate group present at each end of the polyurethane prepolymer chains.

The water-insoluble and non-water dispersible isocyanate functionalized polyurethane prepolymer is substantially free of ionic group and/or group of ion source, i.e., ionic group and/or group of ion source are preferably present in a content of less than 15 mEq/100 g of polyurethane prepolymer, further preferably of less than 5 mEq/100 g of polyurethane prepolymer, more preferably of less than 1 mEq/100 g of polyurethane prepolymer, and most preferably of less than 0.1 mEq/100 g of polyurethane prepolymer. Here water refers to deionized water without surfactants added.

The water-insoluble and non-water dispersible isocyanate functionalized polyurethane prepolymer can be prepared by reacting a system comprising a polyol and an organic polyisocyanate.

Polyol

The polyol may be one or more selected from the group consisting of: polyether polyol, polycarbonate polyol, polyether polycarbonate polyol and polyester polyol; most preferably the polyol with linear structure.

The polyol has preferably a number-average molecular weight of 400-6000 g/mol and most preferably of 600-3000 g/mol.

The polyol may have a hydroxyl functionality of 1.5-6, further preferably of 1.8-3, and most preferably of 1.9-2.1.

The polyol with linear structure is preferably one or more selected from the group consisting of: polytetramethylene glycol polyether and polycarbonate polyol, most preferably polytetramethylene glycol polyether. Furthermore, the polyol is preferably selected from the well-known group of polyesterpolyols.

Organic Polyisocyanate

The isocyanate group (NCO) functionality of the organic polyisocyanate is preferably no less than 2.

The organic polyisocyanate is preferably one or more selected from the group consisting of: aliphatic polyisocyanate, aromatic polyisocyanate and cycloaliphatic polyisocyanate.

The organic polyisocyanate is most preferably one or more selected from the group consisting of: 1,4-butylene diisocyanate, 1,6-hexamethylene diisocyanate(HDI), isophorone diisocyanate(IPDI), 2,2,4- and/or 2,4,4-trimethyl hexamethylene diisocyanate, dis(4,4'-isocyanatocyclohexyl)methane isomers or mixtures of such isomers, 1,4-cyclohexylene diisocyanate, 4-isocyanatomethyl-1,8-octane diisocyanate (nonane triisocyanate), 1,4-phenylene diisocyanate, 2,4- and/or 2,6-toluene diisocyanate, 1,5-naphthalene diisocyanate, 2,2'- and/or 2,4'- and/or 4,4'-diphenylmethane diisocyanate, 1,3- and/or 1,4-di(2-isocyanato-prop-2-yl)benzene (TMXDI), 1,3-dnisocyanatomethyl)-benzene(XDI) and alkyl 2,6-diisocyanatohexanoate with $C_1$-$C_8$ alkyl (lysine diisocyanate), most preferably hexamethylene diisocyanate, and/or isophorone diisocyanates. Preferred are also mixtures of at least two of the aforementioned isocyanates. Furthermore preferable, the organic polyisocyanate is at least partly dicyclohexylmethane diisocyanates or a mixture with any of the aforementioned isocyanates.

The organic polyisocyanate may also be selected from the group consisting of those containing heteroatom in the group linked to isocyanate group, for example, those polyisocyanates obtained by structurally modifying uretidione, isocyanurate, carbamate, allophanate, biuret, carbodiimide, iminooxadiazinedione and/or oxadiazinetrione.

The system used to prepare polyurethane prepolymer may further contain hydroxyl-functional compounds with number-average molecular weight of 62-399 g/mol and/or non-ionic hydrophilic agents.

Hydroxyl-Functional Compound with Number-Average Molecular Weight of 62-399 g/mol The hydroxyl-functional compound with number-average molecular weight of 62-399 g/mol may be one or more selected from the group consisting of: non-polymeric polyol with no more than 20 carbon atoms, ester diol and mono-functional hydroxyl compound.

The non-polymeric polyol with no more than 20 carbon atoms may be one or more selected from the group consisting of: ethylene glycol, diethylene glycol, triethylene glycol, 1,2-propanediol, 1,3-propanediol, 1,4-butanediol, 1,3-butanediol, cyclohexanediol, 1,4-cyclohexanedimethanol, 1,6-hexanediol, neopentyl glycol, hydroquinone dihydroxy ethyl ether, bisphenol A (2,2-bis(4-hydroxyphenyl)propane), hydrogenated bisphenol A (2,2-bis(4-hydroxycyclohexyl)propane), trimethylolpropane, trimethylolethane, glycerol and pentaerythritol.

The ester diol may be one or more selected from the group consisting of: α-hydroxybutyl ε-hydroxyhexanoate, ω-hydroxyhexyl γ-hydroxybutyrate, (β-hydroxyethyl) adipate and bis(β-hydroxyethyl) terephthalate.

The mono-functional hydroxyl compound may be one or more selected from the group consisting of: ethanol, n-butyl alcohol, ethylene glycol monobutyl ether, diethylene glycol monomethyl ether, diethylene glycol monobutyl ether, propylene glycol monomethyl ether, dipropylene glycol monomethyl ether, tripropylene glycol monomethyl ether, dipropylene glycol monopropyl ether, propylene glycol monobutyl ether, dipropylene glycol monobutyl ether, tripropylene glycol monobutyl ether, 2-ethylhexanol, 1-octanol, 1-dodecanol and 1-hexadecanol.

Non-Ionic Hydrophilic Agent

The non-ionic hydrophilic agent may be one or more selected from the group consisting of: polyoxyalkylene ethers containing hydroxyl, amino and thiol groups.

Preferably, the non-ionic hydrophilic agent is mono-hydroxyl functionalized polyoxyalkylene polyether containing 5-70, preferably 7-55 ethylene oxide units/molecule. The polyoxyalkylene polyether may be obtained by oxyalkylation of suitable starting molecules in accordance with known methods.

The mono-hydroxyl functionalized polyoxyalkylene polyether may be either pure polyoxyethylene polyether or mixed polyoxyalkylene polyether, which contains no less than 30 mol %, preferably no less than 40 mol % of ethylene oxide units, based on that the amount of oxyalkylene units is 100 mol %.

Isocyanate Reactive Compound

The isocyanate reactive compound may be one or more selected from the group consisting of: amino functional compounds and hydroxyl functional compounds.

The amino functional compound may be one or more selected from the group consisting of: primary amines, secondary amines and diamines, particularly preferably diamines.

The amino functional compound is further preferably selected from the group consisting of: amino functional compounds without ionic group or group of ion source; and amino functional compounds with ionic group(s) or group(s) of ion source.

The amino functional compound without ionic group or group of ion source may be one or more selected from the group consisting of: organic diamines, polyamines, compounds containing primary and secondary amino groups, compounds containing (primary or secondary) amino and hydroxyl group(s), and mono-functional isocyanate reactive amine compounds.

The organic diamine may be one or more selected from the group consisting of: 1,2-ethanediamine, 1,2- and 1,3-diaminopropane, 1,4-diaminobutane, 1,6-diaminohexane, isophorone diamine, isomer mixtures of 2,2,4- and 2,4,4-trimethylhexamethylenediamine, 2-methylpentamethylenediamine, 4,4-diaminodicyclohexylmethane, hydrazine hydrate and dimethylethylenediamine.

The polyamine may be diethylenetriamine.

The compound containing primary and secondary amino groups may be one or more selected from the group consisting of: diethanolamine, 3-amino-1-methylaminopropane, 3-amino-1-ethylaminopropane, 3-amino-1-cyclohexylaminopropane and 3-amino-1-methylaminobutane.

The alkanolamine containing (primary or secondary) amino and hydroxyl group(s) may be one or more selected from the group consisting of: N-aminoethylethanolamine, ethanolamine, 3-aminopropanol and neopentanolamine.

The mono-functional isocyanate reactive amine compound may be one or more selected from the group consisting of: methylamine, ethylamine, propylamine, butylamine, octylamine, laurylamine, stearylamine, isononyloxypropylamine, dimethylamine, diethylamine, dipropylamine, dibutylamine, N-methylaminopropylamine, diethyl(methyl)aminopropylamine, morpholine, piperidine and their suitable substituted derivatives.

The amino functional compound without ionic group or group of ion source is most preferably one or more selected from the group consisting of: 1,2-ethanediamine, bis(4-aminocyclohexyl)methane, 1,4-diaminobutane, isophorone diamine, ethanolamine, diethanolamine and diethylenetriamine.

The amino functional compound with ionic group(s) or group(s) of ion source may be an anionic hydrophilic compound.

The anionic hydrophilic compound may be one or more selected from the group consisting of: 2-(2-aminoethylamino)ethanesulfonic acid, ethanediamine-propyl- or -butyl-sulfonic acid, 1,2- or 1,3-propanediamine-β-ethylsulfonic acid and taurine, and salts thereof.

The anionic hydrophilic compound is most preferably selected from those containing an sulfonate group as ionic group and containing two amino groups, for example 2-(2-aminoethylamino)ethylsulfonate and/or 1,3-propanediamine-β-ethylsulfonate.

The hydroxyl functional compound may be polymeric polyol.

The polymeric polyol may be one or more selected from the group consisting of: polyester polyol, polyacrylate polyol, polyurethane polyol, polycarbonate polyol, polyether polyol, polyester polyacrylate polyol, polyurethane polyacrylate polyol, polyurethane polyester polyol, polyurethane polyether polyol, polyurethane polycarbonate polyol and polyester polycarbonate polyol; preferably one or more selected from the group consisting of: polytetramethylene glycol polyether and polycarbonate polyol; most preferably polytetramethylene glycol polyether polyol.

The anionic polyurethane may be added to the system as a solid or a dispersion, preferably as a dispersion, i.e., as an aqueous polyurethane dispersion. The anionic polyurethane added to the system as a solid may be dispersed in the water in the system to form an anionic aqueous polyurethane dispersion.

For materials in the form of a dispersion, weight of active material=weight of the dispersion×the content of the solid component in the dispersion. For solid materials containing crystal water, weight of active material=weight of the material−weight of the crystal water.

Preparation of Anionic Aqueous Polyurethane Dispersion

The anionic aqueous polyurethane dispersion is prepared as follows:
preparing the water-insoluble, non-water dispersible isocyanate functionalized polyurethane prepolymer;
reacting the polyurethane prepolymer with the isocyanate reactive compound; and
dispersing the anionic polyurethane in water before, during or after the reaction.

The anionic groups contained in the anionic aqueous polyurethane dispersion are introduced by the amino functional compound with ionic group(s) or group(s) of ion source among the isocyanate reactive compounds.

The preparation of the anionic aqueous polyurethane dispersion can be performed in homogeneous phase in one or more stages, or partially in dispersed phase for reaction with multiple stages. The preparation method for the anionic aqueous polyurethane dispersion may be prepolymer mixing method, acetone method or melt dispersing method, preferably the acetone method.

The equivalent ratio of the isocyanate groups to the isocyanate reactive groups is preferably 1.05-3.5, further preferably 1.1-3.0, and most preferably 1.1-2.5.

The anionic aqueous polyurethane has a particle diameter preferably of less than 750 nm and most preferably of less than 500 nm. The particle diameter according to the present invention is obtained by diluting the anionic aqueous polyurethane with deionized water followed by determining with Malvern Zetasizer 1000 from the company Malver.

The anionic aqueous polyurethane dispersion has a solid content of 10-70 wt %, preferably of 30-65 wt %, and most preferably of 40-60 wt %, based on that the amount of the anionic aqueous polyurethane dispersion is 100 wt %. The solid content is calculated by heating the weighed sample at 125° C. until a constant weight is achieved and then weighing the sample again.

The anionic aqueous polyurethane dispersion is preferably one or more selected from the group consisting of: Baycusan® C1000, Baycusan® C1001, Baycusan® C1003, Baycusan® C1004, Baycusan® C1005 and Baycusan® C1008; most preferably one or more selected from the group consisting of: Baycusan® C1000 and Baycusan® C1004. Also, Baycusan® C1010 is preferred as anionic aqueous polyurethane dispersion.

Amphoteric Polymer

The amphoteric polymer of the present invention refers to those polymer bearing both anionic group(s) and cationic group(s).

The amphoteric polymer is preferably present in an amount of 0.1-10 wt %, further preferably of 0.5-10 wt % and most preferably of 0.5-1 wt %, based on that the amount of the composition is 100 wt %.

The amount of the above amphoteric polymer refers to the actual weight of the active material of the amphoteric polymer, excluding the carrier.

Preferably, the amphoteric polymer is an amphoteric polyquaternium.

Preferably, the amphoteric polyquaternium is one or more selected from the group consisting of: Polyquaternium-39 (copolymer of dimethyl diallyl ammonium chloride, acrylamide and acrylic acid) and Polyquaternium-51. Furthermore, the amphoteric polyquaternium preferably comprises Polyquaternium-74.

The amphoteric polymer may be added to the system as a solid or a dispersion, preferably as a dispersion, i.e., as an amphoteric polymer dispersion. The amphoteric polymer added to the system as a solid may be dispersed in the water in the system to form the amphoteric polymer dispersion.

Preferably, the weight ratio of the anionic polymer to the amphoteric polymer is in the range from 1:50 to 50:1, preferably from 1:10 to 50:1 and most preferably from 1:1 to 5:1.

The total weight of the anionic polymer and the amphoteric polymer is preferably no less than 0.1 wt % and no more than 10 wt %, based on that the amount of the composition is 100 wt %.

The total weight of the anionic polymer and the amphoteric polymer is most preferably no less than 0.5 wt % and no more than 5 wt %, based on that the amount of the composition is 100 wt %.

Cationic Polymer

The cationic polymer may further increase the deposition amount of the composition on the hair.

The cationic polymer may be one or more selected from the group consisting of: cassia hydroxypropyl trimethyl ammonium chloride, Polyquaternium-7(PQ-7), Polyquaternium-10(PQ-10), hexadecyl trimethyl ammonium chloride, octadecyl trimethyl ammonium chloride, docosyl trimethyl ammonium chloride, dioctadecyl dimethyl ammonium chloride, guar hydroxypropyl trimethyl ammonium chloride, higher alcohols, lanolin, squalane and phytosterol. Also, behentrimonium chloride is preferred as cationic polymer.

Further preferable cationic polymers are selected from the group of cationic synthetic polymer such as Polyquaternium-7, Polyquaternium-11, Polyquaternium-46 or Polyquaternium-55, quaternary guar derivatives (e.g. Guar Hydroxypropyl Trimonium Chloride), quaternary cellulose derivatives (e.g. Polyquaternium-4 or polyquaternium-10), quaternized protein, chitosan derivatives (e.g. Polyquaternium-29), starch derivatives, quaternized silicon (e.g. Polyquaternium-42) or mixtures of at least two thereof.

The cationic polymer is most preferably one or more selected from the group consisting of: Polyquaternium-39 (PQ-39), squalane, phytosterol and docosyl trimethyl ammonium chloride. Further preferred cationic polymers are behentrimonium Chloride, Polyquaternium-4, polyquaternium-7, polyquaternium-10 and polyquaternium-11 or mixtures of at least two thereof.

The cationic polymer may present in an amount of 0.1-5 wt %, most preferably of 0.5-2 wt %, based on that the amount of the cosmetic composition is 100 wt %.

The amount of the above cationic polymer refers to the actual weight of the active material of the cationic polymer, excluding the carrier.

The cationic polymer may be added to the cosmetic composition as a solid or a dispersion.

Active Ingredient

The active ingredient may be selected from functional ingredients well known to those skilled in the art that can be added to the cosmetic composition. By "functional", we mean moisturizing, softening, nourishing, skin conditioning, anti-microbial, anti-oxidative etc.

The active ingredient may be one or more selected from the group consisting of: glutamic acid, fucose, pyrrolidone carboxylic acid, hydrolyzed rice protein, honey, sodium hyaluronate, 2-oleamido-1,3-octadecanediol (one of the ceramides), jojoba oil, palm oil, olive oil, squalane, perilla extract, zostera marina extract, hypnea musciformis extract, levisticum officinale root extract, rosa alba flower extract, luffa cylindrica fruit extract, *Coffea arabica* seed extract and aloe extract.

The amount of the active ingredient may be well known to those skilled in the art, and preferably 0.01-10 wt %, further preferably 0.1-5 wt %, and most preferably 0.1-0.5 wt %, based on that the amount of the cosmetic composition is 100 wt %.

Cosmetically Acceptable Medium

The cosmetically acceptable medium may be selected in accordance with other ingredients in the cosmetic composition.

The cosmetically acceptable medium is preferably one or more selected from the group consisting of: water and aqueous solutions of lower alkanols.

The cosmetically acceptable medium is most preferably water.

The water is preferably deionized water.

The lower alkanol may be monohydric alcohol with 1-6 carbon atoms.

The monohydric alcohol with 1-6 carbon atoms may be one or more selected from the group consisting of: ethanol and isopropanol.

The amount of the cosmetically acceptable medium may be well known to those skilled in the art, and preferably 20-99 wt %, further preferably 30-99 wt %, and most preferably 40-80 wt %, based on that the amount of the cosmetic composition is 100 wt %.

Surfactant

The surfactant may be one or more selected from the group consisting of: cationic surfactants, anionic surfactants, amphoteric surfactants and non-ionic surfactants.

The surfactant is most preferably an anionic surfactant.

The anionic surfactant may be one or more selected from the group consisting of: sodium fatty alcohol polyoxyethylene ether sulfate and ammonium fatty alcohol polyoxyethylene ether sulfate.

The anionic surfactant may be one or more selected from the group consisting of: sodium N-lauroyl-L-glumate and sodium lauroyl sarcosinate LS-30, most preferably sodium N-lauroyl-L-glumate.

The amphoteric surfactant may be one or more selected from the group consisting of: cocoamidopropyl betaine, lauramidohydroxysultaine and lauroamphoacetate.

The non-ionic surfactant may be decyl glucoside.

The amount of the surfactant may be well known to those skilled in the art, and preferably 0.1-5 wt %, further preferably 1-3 wt %, based on that the amount of the cosmetic composition is 100 wt %.

Thickening Agent

The cosmetic composition may further comprise a thickening agent.

The thickening agent may be present in the cosmetic composition as a solid or a dispersion.

The thickening agent may be one or more selected from the group consisting of: NaCl, $NH_4Cl$, hydroxyethyl cellulose, hydroxypropyl methyl cellulose, acrylic acid and acrylate Copolymer, most preferably hydroxyethyl cellulose.

The amount of the thickening agent may be well known to those skilled in the art, and preferably 0.1-5 wt %, further preferably 0.5-5 wt %, and most preferably 1-3 wt %, based on that the amount of the cosmetic composition is 100 wt %.

Preservative

The cosmetic composition may further comprise a preservative.

The preservative may be those well known to those skilled in the art that can be used in the field of cosmetics.

The preservative may be one or more selected from the group consisting of: dimethylol dimethylhydantoin, methylisothiazolinone, ethylhexylglycerin, methylparaben, ethylparaben, propylparaben, butylparaben, isobutylparaben, benzalkonium chloride, bronopol, chlorhexidine, chlorocresol and derivatives thereof, ethanol, phenoxyethanol, potassium sorbate, diazonium imidazolidinyl urea, benzyl alcohol and p-hydroxybenzoate.

The amount of the preservative may be 0.1-1 wt %, preferably 0.2-0.8 wt %, and most preferably 0.2-0.5 wt %, based on that the amount of the cosmetic composition is 100 wt %.

Additive

The additive of the present invention may be selected from those physically and chemically compatible with various ingredients present in the cosmetic composition according to the present invention.

The additive may be one or more selected from the group consisting of: co-emulsifiers, dyestuffs, non-volatile solvents, diluents, nacreous agents, foam boosters, additional surfactants, non-ionic co-surfactants, lousicides, pH adjusters, fragrances, chelating agents, proteins, skin actives, sunscreens, ultraviolet light absorbers and vitamins.

The amount of the additive may be well known to those skilled in the art, and preferably 0.01-25 wt %, based on that the amount of the cosmetic composition is 100 wt %.

Preparation Method of the Cosmetic Composition

The reaction may be flocculation.

The reaction is preferably performed at ambient temperature and under atmospheric pressure.

The cosmetically acceptable medium, active material, thickening agent, preservative and additive can either be added to the system directly independent of each other or mixed with the polymerization product after it is produced.

Cleaning and Caring Product

The cleaning and caring product is a shampoo or a conditioner.

Method for Hair Care

The method for hair care may also include applying the cleaning and caring product comprising the aqueous anionic polyurethane dispersion and the cleaning and caring product comprising the amphoteric polymer onto hair surface, respectively, thus forming a polymerization product on the hair surface directly. It should be noted that, cationic polymer is required to be added after formation of the polymerization product, otherwise it will polymerize with the aqueous anionic polyurethane dispersion, which will have an adverse impact on the effect of the composition according to the present invention.

Examples

Unless defined otherwise, all the technical and scientific terms used herein have the same meanings as those commonly understood by those skilled in the art to which the present invention pertains. In the case that the definition of a term in the specification conflicts with that commonly understood by those skilled in the art to which the present invention pertains, the definition described herein controls.

Unless indicated otherwise, all the numerical values used in the description and claims to express the amounts of ingredients, reaction conditions and so on should be understood to be modified by the term "about". Therefore, unless indicated otherwise, the numerical parameters set forth herein are approximations that can be varied depending on the desired properties required.

As used herein, the "and/or" means one or all of the elements referred to.

As used herein, the "include" and "comprise" encompass both the cases wherein only the elements mentioned exist and the cases whereinother elements that are not mentioned in addition to the elements mentioned exist.

Unless indicated otherwise, all the percentages in the present invention are % by weight and based on that the amount of the cosmetic composition according to the present invention is 100%.

Unless indicated otherwise, the molecular weight according to the present invention is number-average molecular weight. The number-average molecular weight is determined with gel permeation chromatography (GPC) in accordance with GB/T 21863-2008<Gel Permeation Chromatography (GPC) Tetrahydrofuran as Elution Solvent>.

Unless indicated otherwise, all the analytical measurements are performed at 23±2° C.

The solid content of the aqueous polyurethane dispersion is determined with HS153 Moisture Tester from the company Mettler Toledo according to DIN-EN ISO 3251.

The content of hydroxyl groups is determined according to ASTM D4274.

The content of amine groups is determined according to AFAM 2011-06054.

The content of isocyanate groups (NCO) is determined as volume according to DIN-EN ISO 11909 and the data determined includes the contents of both free and potentially free NCO.

The isocyanate functionality is determined according to GPC.

Raw Materials and Reagents

Baycusan® C1004: anionic aqueous polyurethane dispersion, solid content: 50 wt %, INCI name: Polyurethane-35, available from Covestro Polymers (China) Company Limited.

Polyquaternium-39: dimethyl diallyl ammonium chloride-acrylamide-acrylic acid copolymer (PQ-39), solid content: 10 wt %, used as the amphoteric polyquaternium in the cosmetic composition of the present invention, available from Lubrizol Specialty Chemicals (China) Co., Ltd.

Sodium N-lauroyl-L-glumate: white powder, active material content: 93 wt %, used as the anionic surfactant in the cosmetic composition of the present invention, available from Lubrizol Specialty Chemicals (China) Co., Ltd.

Docosyl trimethyl ammonium chloride: used as the cationic polymer in the cosmetic composition of the present invention, solid content: 85 wt %, available from Lubrizol Specialty Chemicals (China) Co., Ltd.

Cetostearyl alcohol: white lamellar solid, used as the co-emulsifier in the cosmetic composition of the present invention, available from Guangzhou Flower King Chemicals Co., Ltd.

Hydroxyethyl cellulose (HEC): used as the thickening agent in the cosmetic composition of the present invention, available from Guangzhou Flower King Chemicals Co., Ltd.

Hydrolyzed wheat protein peptide: used as the active ingredient in the cosmetic composition of the present invention, available from Ganzhou Baizhentang Biotech Co., Ltd.

Jojoba oil: colorless oily liquid, used as the active ingredient in the cosmetic composition of the present invention, available from Guangzhou Yazhi Cosmetics Co., Ltd.

Perilla extract: colorless or amber clear and transparent liquid, solid content: 2.5 wt %, used as the active ingredient in the cosmetic composition of the present invention, available from Guangzhou Fuliangye Chemicals Co., Ltd.

Aloe extract: colorless transparent liquid, used as the active ingredient in the cosmetic composition of the present invention, available from Guangzhou Meiyi Biotech Co., Ltd.

Pantene conditioner: Moisturizing & Repair Conditioner lotion type.

Head & Shoulders shampoo: Anti-Dandruff Shampoo (Oil Control) type.

Hair locks: all the hair locks used in the Examples and Comparative Examples according to the present invention are human hair. The locks are healthy, not permed and/or dyed and each has substantially the same quality and color.

Preparation Method of Cosmetic Compositions of Examples 1-4

Baycusan® C1004 and Polyquaternium-39 were mixed homogenously at room temperature and under atmospheric pressure according to the compositions and contents shown in Table 1, and reacted to obtain a polymerization product. The cationic polymer, surfactant and additives were dissolved in water with heating by water bath at 70° C., cooled down to room temperature and then mixed with the polymerization product, then the active ingredients are added to form the cosmetic compositions.

Preparation Method of Cosmetic Compositions of Comparative Examples 1-7

According to the compositions and contents shown in Table 1, the cationic polymer, surfactant and additives were dissolved in water with heating by water bath at 70° C., cooled down to room temperature and then Baycusan® C1004, Polyquaternium-39 and active ingredient are added successively, to form the comparative cosmetic compositions.

TABLE 1

Compositions and Contents of the Cosmetic Compositions of the Inventive Examples and Comparative Examples/Unit: g

| | Ex. 1 | Ex. 2 | Ex. 3 | Ex. 4 | Com. Ex. 1 | Com. Ex. 2 | Com. Ex. 3 | Com. Ex. 4 | Com. Ex. 5 | Com. Ex. 6 | Com. Ex. 7 |
|---|---|---|---|---|---|---|---|---|---|---|---|
| Baycusan ® C1004 | 1 | 2 | 3 | 5 | 1 | 2 | 3 | 5 | 0 | 5 | 0 |
| Polyquaternium-39 | 10 | 10 | 9 | 5 | 10 | 10 | 9 | 5 | 5 | 0 | 0 |
| Sodium N-lauroyl-L-glumate | 3.0 | 3.0 | 3.0 | 3.0 | 3.0 | 3.0 | 3.0 | 3.0 | 3.0 | 3.0 | 3.0 |
| Docosyl trimethyl ammonium chloride | 1.0 | 1.0 | 1.0 | 1.0 | 1.0 | 1.0 | 1.0 | 1.0 | 1.0 | 1.0 | 1.0 |
| Cetostearyl alcohol | 2.0 | 2.0 | 2.0 | 2.0 | 2.0 | 2.0 | 2.0 | 2.0 | 2.0 | 2.0 | 2.0 |
| Hydroxyethyl cellulose | 3.0 | 3.0 | 3.0 | 3.0 | 3.0 | 3.0 | 3.0 | 3.0 | 3.0 | 3.0 | 3.0 |
| Hydrolyzed wheat protein peptide | 0.1 | 0.1 | 0.1 | 0.1 | 0.1 | 0.1 | 0.1 | 0.1 | 0.1 | 0.1 | 0.1 |
| Jojoba oil | 0.2 | 0.2 | 0.2 | 0.2 | 0.2 | 0.2 | 0.2 | 0.2 | 0.2 | 0.2 | 0.2 |
| *Perilla* extract | 0.2 | 0.2 | 0.2 | 0.2 | 0.2 | 0.2 | 0.2 | 0.2 | 0.2 | 0.2 | 0.2 |
| Water | QS | QS | QS | QS | QS | QS | QS | QS | QS | QS | QS |
| Total Weight | 100 | 100 | 100 | 100 | 100 | 100 | 100 | 100 | 100 | 100 | 100 |

Note: all the above weights include the weight of the carrier.

Softness and Combability Test of Hair Locks Sample

The hair locks were immersed into sodium lauryl ether sulfate, then taken out and immersed in ethanol for 24 hours, taken out and finally dried in the oven at 40° C. for 24 hours, to obtain clean hair locks samples.

0.5 g of the cosmetic composition of Examples or Comparative Examples was weighed and applied to the surface of the clean hair locks sample. After 5 minutes, the hair locks were rinsed with water for 2 minutes, then left to dry at room temperature for 24 hours. Then, the hair locks were combed with a comb, with each being combed for the same times. The softness and combability of the samples were evaluated and the results were summarized in Table 2. Combability according to the invention means the ability to comb the hair.

TABLE 2

Softness and Combability Test Results of Hair Locks Sample Treated with the Cosmetic Compositions of the Inventive Examples and Comparative Examples

| | Softness | Combability |
|---|---|---|
| Ex. 1 | soft & smooth | easy to comb |
| Ex. 2 | soft & smooth | easy to comb |
| Ex. 3 | soft & smooth | easy to comb |
| Ex. 4 | soft & smooth | easy to comb |
| Com. Ex. 1 | relatively dry & more resistance | tend to tangle |
| Com. Ex. 2 | relatively dry & more resistance | tend to tangle |
| Com. Ex. 3 | relatively dry & more resistance | tend to tangle |
| Com. Ex. 4 | relatively dry & more resistance | tend to tangle |
| Com. Ex. 5 | relatively soft | tend to tangle |
| Com. Ex. 6 | relatively dry & more resistance | easy to tangle |
| Com. Ex. 7 | relatively coarse and rigid | easy to tangle |

From Table 2, it can be seen that hair locks treated with the cosmetic compositions of Examples 1-4 were soft, smooth and easy to comb. However, the hair locks treated with the cosmetic compositions of Comparative Examples 1-7 were dry and more resistance, coarse and easy to tangle. Therefore, the effect resulted from application of the cosmetic composition of Examples to the hair locks sample was superior to that resulted from application of the comparative cosmetic composition of Comparative Examples to the hair locks sample, thus demonstrating that the deposition amount of the active ingredients in the cosmetic compositions of the inventive Examples on the hair was higher than that of Comparative Examples.

User Experience Test

Forty-nine users of 25 to 65 years old were selected randomly to participate in the user experience test. The hair of the users was applied with the cosmetic compositions of the inventive Examples and Comparative Examples and then rinsed with water. The wet combing, shine under wet state, dry combing, shine under dry state and elastic force/volume were evaluated and scored by the users respectively. The highest score for each test was 5 points and the lowest was 1 point. The comprehensive score by each user was calculated and the results were summarized in Table 3.

TABLE 3

Results of User Experience Test

| | Wet Combing | Shine Under Wet State | Dry Combing | Shine Under Dry State | Elastic Force/Volume | Comprehensive Score |
|---|---|---|---|---|---|---|
| Ex. 1 | 4.6 | 4.3 | 4.0 | 4.0 | 3.8 | 4.14 |
| Ex. 2 | 4.8 | 4.7 | 4.5 | 4.5 | 4.1 | 4.52 |

TABLE 3-continued

Results of User Experience Test

|  | Wet Combing | Shine Under Wet State | Dry Combing | Shine Under Dry State | Elastic Force/Volume | Comprehensive Score |
|---|---|---|---|---|---|---|
| Ex. 3 | 5.0 | 4.8 | 5.0 | 4.8 | 4.8 | 4.88 |
| Ex. 4 | 4.1 | 4.2 | 4.2 | 4.3 | 4.3 | 4.22 |
| Com. Ex. 1 | 3.5 | 3.7 | 3.8 | 3.6 | 3.7 | 3.66 |
| Com. Ex. 2 | 3.1 | 3.2 | 3.2 | 3.5 | 3.6 | 3.32 |
| Com. Ex. 3 | 3.0 | 3.1 | 3.4 | 3.4 | 3.3 | 3.24 |
| Com. Ex. 4 | 3.0 | 3.2 | 3.2 | 3.4 | 3.3 | 3.22 |
| Com. Ex. 5 | 3.6 | 3.5 | 3.5 | 3.6 | 3.4 | 3.52 |
| Com. Ex. 6 | 3.2 | 3.3 | 3.2 | 3.4 | 3.0 | 3.22 |
| Com. Ex. 7 | 3.2 | 3.0 | 3.1 | 3.1 | 3.2 | 3.12 |

From Table 3, it can be seen that the comprehensive scores of the user experience test of the hair treated with the cosmetic compositions of the inventive Examples 1-4 were substantially higher than those of the hair treated with the cosmetic compositions of Comparative Examples 1-7. Therefore, the effect resulted from application of the cosmetic composition of the inventive Examples to the hair was superior to that resulted from application of the comparative cosmetic composition of Comparative Examples to the hair, thus demonstrating the deposition amount of the active ingredients in the cosmetic compositions of Examples on the hair was higher than that of Comparative Examples.

Stability Test

The cosmetic compositions of the inventive Examples and Comparative Examples were stored at various temperatures, i.e., 45° C., room temperature and −15° C., respectively, for one month and then the aspect of the compositions was observed. If the composition showed no delamination and no significant change, it was considered stable; whereas if the composition flocculated and even agglomerated, it was considered unstable. The results were summarized in Table 4.

TABLE 4

Stability Test Results of the Cosmetic Compositions of the Inventive Examples and Comparative Examples

|  | 45° C. | Room Temperature | −15° C. |
|---|---|---|---|
| Ex. 1 | no delamination & no significant change | no delamination & no significant change | no delamination & no significant change |
| Ex. 2 | no delamination & no significant change | no delamination & no significant change | no delamination & no significant change |
| Ex. 3 | no delamination & no significant change | no delamination & no significant change | no delamination & no significant change |
| Ex. 4 | no delamination & no significant change | no delamination & no significant change | no delamination & no significant change |
| Com. Ex. 1 | flocculated | flocculated | agglomerated |
| Com. Ex. 2 | flocculated | flocculated | agglomerated |
| Com. Ex. 3 | flocculated | flocculated | agglomerated |
| Com. Ex. 4 | flocculated | flocculated | agglomerated |
| Com. Ex. 5 | no delamination & no significant change | no delamination & no significant change | no delamination & no significant change |
| Com. Ex. 6 | flocculated | flocculated | agglomerated |
| Com. Ex. 7 | no delamination & no significant change | no delamination & no significant change | no delamination & no significant change |

From Table 4, it can be seen that after the cosmetic compositions of the inventive Examples were stored at 45° C., room temperature and −15° C. for one month, they showed no delamination and no significant change and thus were stable. However, after the comparative cosmetic compositions of the Comparative Examples were stored at 45° C., room temperature and −15° C. for one month, they would flocculate and even agglomerate and thus not stable enough.

Deposition Test of the Active Ingredients—Conditioner

Three types of conditioners were prepared as follows:

Conditioner 1: formed by mixing the Pantene conditioner and deionized water, with a weight ratio of 97:3;

Conditioner 2: firstly, Baycusan® C1004 and PQ-39 (weight ratio: 10:1, weights of Baycusan® C1004 and PQ-39 were both those including the weight of the water) were mixed and reacted at room temperature and under atmospheric pressure, to obtain a polymerization product; then the Pantene conditioner, deionized water and the polymerization product (weight ratio: 97:2:1) were mixed to obtain Conditioner 2;

Conditioner 3: firstly, Baycusan® C1004 and PQ-39 (weight ratio: 10:1, weights of Baycusan® C1004 and PQ-39 were both those including the weight of the water) were mixed and reacted at room temperature and under atmospheric pressure, to obtain a polymerization product; then the Pantene conditioner and the polymerization product (weight ratio: 97:3) were mixed to obtain Conditioner 3.

Hair locks were treated with the conditioners as follows:

The hair locks were immersed into sodium lauryl ether sulfate, then taken out and immersed in ethanol for 24 hours, taken out and finally dried in the oven at 40° C. for 24 hours, to obtain a clean hair locks sample.

The clean hair locks sample was weighed to obtain the weight before applying the conditioners and the data was shown in Table 5.

0.5 g of the conditioner was weighed and applied to the surface of clean hair locks. After 5 minutes, the hair locks were rinsed with water for 2 minutes, then left to dry at room temperature for 24 hours and weighed to obtain the weight after applying the conditioners and the data was shown in Table 5.

TABLE 5

Weight Comparison of Hair Locks before and after Applying with Conditioners 1-3

|   | Weight of Hair Locks (before applying conditioner)/g | Weight of Hair Locks (after applying conditioner)/g | Deposition amount of Active Ingredient/g | Average Deposition amount of Active Ingredient/g | Deposition Rate of Active Ingredient (average deposition amount of active ingredient/weight of conditioner)/% |
|---|---|---|---|---|---|
| Conditioner 1 | 5.0510 g<br>5.0291 g | 5.0576 g<br>5.0346 g | 0.0066 g<br>0.0055 g | 0.0061 | 1.22% |
| Conditioner 2 | 5.2599 g<br>4.9140 g | 5.2691 g<br>4.9229 g | 0.0081 g<br>0.0079 g | 0.0080 | 1.6% |
| Conditioner 3 | 5.2317 g<br>5.0122 g | 5.2418 g<br>5.0224 g | 0.0101 g<br>0.0102 g | 0.0102 | 2.0% |

From Table 5, it can be seen that both the deposition amount and deposition rate of the active ingredients of Conditioner 2 and Conditioner 3 which comprise the composition of the present invention are superior to those of Conditioner 1.

Deposition Test of the Active Ingredients—Shampoo

Three types of shampoos were prepared as follows:

Shampoo 1: formed by mixing the Head & Shoulders shampoo and deionized water, with a weight ratio of 97:3;

Shampoo 2: formed by mixing the Head & Shoulders shampoo and Baycusan® C1004, with a weight ratio of 97:3 (weight of Baycusan® C1004 was that including the weight of the water);

Shampoo 3: firstly, Baycusan® C1004 and PQ-39(weight ratio: 10:1, weights of Baycusan® C1004 and PQ-39 were both those including the weight of the water) were mixed and reacted at room temperature and under atmospheric pressure, to obtain a polymerization product; then the Head & Shoulders shampoo and the polymerization product (weight ratio: 97:3) were mixed to obtain Shampoo 3.

Hair locks were treated with the shampoos as follows:

The hair locks were immersed into sodium lauryl ether sulfate, then taken out and immersed in ethanol for 24 hours, taken out and finally dried in the oven at 40° C. for 24 hours, to obtaining a clean hair locks sample.

The clean hair locks sample was weighed to obtain the weight before applying the shampoos and the data was shown in Table 6.

1 g of the shampoo was weighed and applied to the surface of clean hair locks. After 5 minutes, the hair locks were rinsed with water for 30 seconds, then left to dry in oven at 40° C. for 24 hours and weighed to obtain the weight after applying the shampoos and the data was shown in Table 6.

TABLE 6

Comparison of Weight of Hair Locks before and after Applying with Shampoos 1-3

|   | Weight of Hair Locks (before applying of shampoo)/g | Weight of Hair Locks (after applying shampoo)/g | Deposition amount of Active Ingredient/g | Average Deposition amount of Active Ingredient/g | Deposition Rate of Active Ingredient (average deposition amount of active ingredient/weight shampoo)/% |
|---|---|---|---|---|---|
| Shampoo 1 | 16.6869<br>16.2839 | 16.8971<br>16.3946 | 0.2102<br>0.1107 | 0.1605 | 16.05 |
| Shampoo 2 | 15.3486<br>16.5567 | 15.5474<br>16.7223 | 0.1988<br>0.1656 | 0.1822 | 18.22 |
| Shampoo 3 | 16.8060<br>15.8614 | 17.0922<br>16.0845 | 0.2862<br>0.2231 | 0.2546 | 25.46 |

From Table 6, it can be seen that both the deposition amount and deposition rate of the active ingredients of Shampoo 3 which comprises the composition of the present invention are superior to those of Shampoo 1 and Shampoo 2.

Microscope Observation:

The hair locks samples treated with Shampoo 1 and Shampoo 3 were placed under microscope and observed respectively. Ten pieces of hair were selected randomly, and the active ingredient zinc pyrithione in the Head & Shoulders shampoo deposited on the hair was marked with box. The results were shown in FIG. 1 and FIG. 2.

Figure 1:
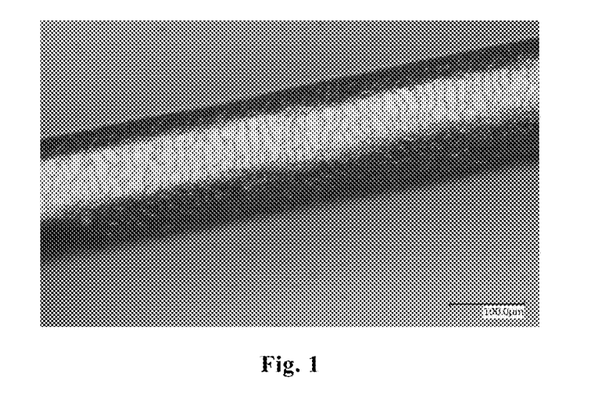
FIG. 1 shows the deposition effect of the active ingredient(s) in Shampoo 1 of the present invention.
Figure 2:
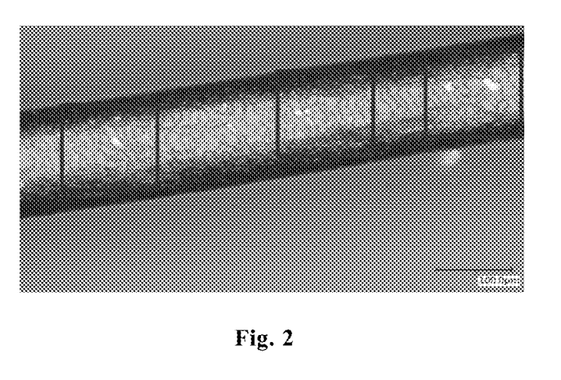
FIG. 2 shows the deposition effect of the active ingredient(s) in Shampoo 3 of the present invention.

The deposition amount of the zinc pyrithione in FIG. 2 was substantially more than that in FIG. 1 and thus it can be seen that the cosmetic composition of the present invention significantly improved the deposition amount of the active ingredient on the hair.

It will be obvious to those skilled in the art to which the present invention pertains that the present invention is not merely limited to the aforementioned specific details and may be practiced as other specific forms without departing from the spirit or primary characteristics of the present invention. Therefore, the examples should be deemed as exemplary instead of restrictive from any perspective and the scope of the present invention is indicated by the Claims other than the Description; and therefore, any change should be considered to be included in the present invention as long as it falls within the meaning and scope of the equivalents of the Claims.

The invention claimed is:

1. A cosmetic composition comprising:
 a polymerization product obtained by reacting a system consisting essentially of:

an anionic polymer, wherein the anionic polymer is anionic polyurethane comprising at least one sulfonic acid group, at least one sulfonate group, or a combination thereof, an amphoteric polymer, wherein the amphoteric polymer is an amphoteric polyquaternium, and water, wherein a weight ratio of the anionic polymer to the amphoteric polymer is in a range from 1:100 to 100:1 and a total weight of the anionic polymer and the amphoteric polymer is no less than 0.1 wt %, based on a total weight of the composition;

an optional cationic polymer;

an optional active ingredient;

an optional additive; and an optional cosmetically acceptable medium.

2. The composition according to claim 1, comprising from 0.1-10 wt % of the anionic polymer, based on the total weight of the composition.

3. The composition according to claim 1, comprising from 0.1-10 wt % of the amphoteric polymer, based on the total weight of the composition.

4. The composition according to claim 1, wherein the weight ratio of the anionic polymer to the amphoteric polymer is in the range from 1:50 to 50:1.

5. The composition according to claim 1, wherein the total weight of the anionic polymer and the amphoteric polymer is no less than 0.1 wt % and no more than 10 wt %, based on the total weight of the composition.

6. The composition according to claim 1, wherein the amphoteric polyquaternium is one or more of: Polyquaternium-39 and Polyquaternium-51.

7. The composition according to claim 1, wherein the sulfonate group is a sodium sulfonate group.

8. The composition according to claim 1, comprising the cationic polymer, wherein the cationic polymer comprises one or more of: cassia hydroxypropyl trimethyl ammonium chloride, Polyquaternium-7(PQ-7), Polyquaternium-10(PQ-10), hexadecyl trimethyl ammonium chloride, octadecyl trimethyl ammonium chloride, docosyl trimethyl ammonium chloride, dioctadecyl dimethyl ammonium chloride, guar hydroxypropyl trimethyl ammonium chloride, higher alcohols, lanolin, squalane, and phytosterol.

9. A method for preparing the composition according to claim 1 comprising:

mixing and reacting the system comprising the anionic polymer, the amphoteric polymer and water to obtain the polymerization product; and mixing the polymerization product; an optional cationic polymer; an optional active ingredient; an optional additive; and an optional cosmetically acceptable medium to obtain the composition.

10. A cleaning and caring product prepared from the composition according to claim 1.

11. The cleaning and caring product according to claim 10, wherein the cleaning and caring product is a shampoo or a conditioner.

12. A method for hair care comprising applying the cleaning and caring product according to claim 10 to hair.

* * * * *